(12) United States Patent
Mizuno et al.

(10) Patent No.: US 9,448,179 B2
(45) Date of Patent: Sep. 20, 2016

(54) GAS ANALYZING APPARATUS

(71) Applicant: HORIBA, Ltd., Kyoto-shi, Kyoto (JP)

(72) Inventors: Yusuke Mizuno, Kyoto (JP); Takuji Oida, Kyoto (JP); Misato Arakawa, Kyoto (JP)

(73) Assignee: HORIBA, LTD., Kyoto (JP)

(*) Notice: Subject to any disclaimer, the term of this patent is extended or adjusted under 35 U.S.C. 154(b) by 0 days.

(21) Appl. No.: 14/578,666

(22) Filed: Dec. 22, 2014

(65) Prior Publication Data
US 2015/0185157 A1 Jul. 2, 2015

(30) Foreign Application Priority Data
Dec. 27, 2013 (JP) ................. 2013-273411

(51) Int. Cl.
| | | |
|---|---|---|
| G01N 7/00 | (2006.01) | |
| G01N 21/00 | (2006.01) | |
| G01N 27/00 | (2006.01) | |
| G01N 31/00 | (2006.01) | |
| G01N 33/00 | (2006.01) | |
| G01N 17/00 | (2006.01) | |
| G01N 21/76 | (2006.01) | |

(52) U.S. Cl.
CPC ........ *G01N 21/766* (2013.01); *G01N 33/0026* (2013.01); *G01N 2201/129* (2013.01)

(58) Field of Classification Search
CPC ........ G01N 7/00; G01N 21/00; G01N 27/00; G01N 31/00; G01N 33/00; G01N 17/00; G01N 21/76

USPC ........... 422/50, 83, 85, 86, 91; 436/43, 164, 436/171, 172
See application file for complete search history.

(56) References Cited

U.S. PATENT DOCUMENTS

| | | | | |
|---|---|---|---|---|
| 3,845,309 | A * | 10/1974 | Helm et al. | 250/365 |
| 4,193,963 | A * | 3/1980 | Bruening et al. | 422/52 |
| 4,469,946 | A * | 9/1984 | Tanaka et al. | 250/373 |
| 6,795,178 | B1 * | 9/2004 | Rasanen et al. | 356/311 |

FOREIGN PATENT DOCUMENTS

JP 07-301603 11/1995

* cited by examiner

*Primary Examiner* — Brian J Sines
(74) *Attorney, Agent, or Firm* — Brooks Kushman P.C.

(57) ABSTRACT

A gas analyzing apparatus includes a gas analyzing unit, a luminescence inducing component generating unit, and a measurement signal calculating unit. The gas analyzing unit receives a sample gas containing a component gas and/or a standard gas and the luminescence inducing gas. The gas analyzing unit is configured to output a detection signal based on an intensity of a reaction light generated by the interaction between the component gas and the luminescence inducing component. The luminescence inducing component generating unit generates the luminescence inducing gas by electric discharge generated repeatedly at specified intervals. The measurement signal calculating unit calculates a first measurement signal based on a first detection signal, based on the reaction light generated when the sample gas and the luminescence inducing gas are introduced, and a second detection signal, based on the reaction light generated when the standard gas and the luminescence inducing gas are introduced.

10 Claims, 8 Drawing Sheets

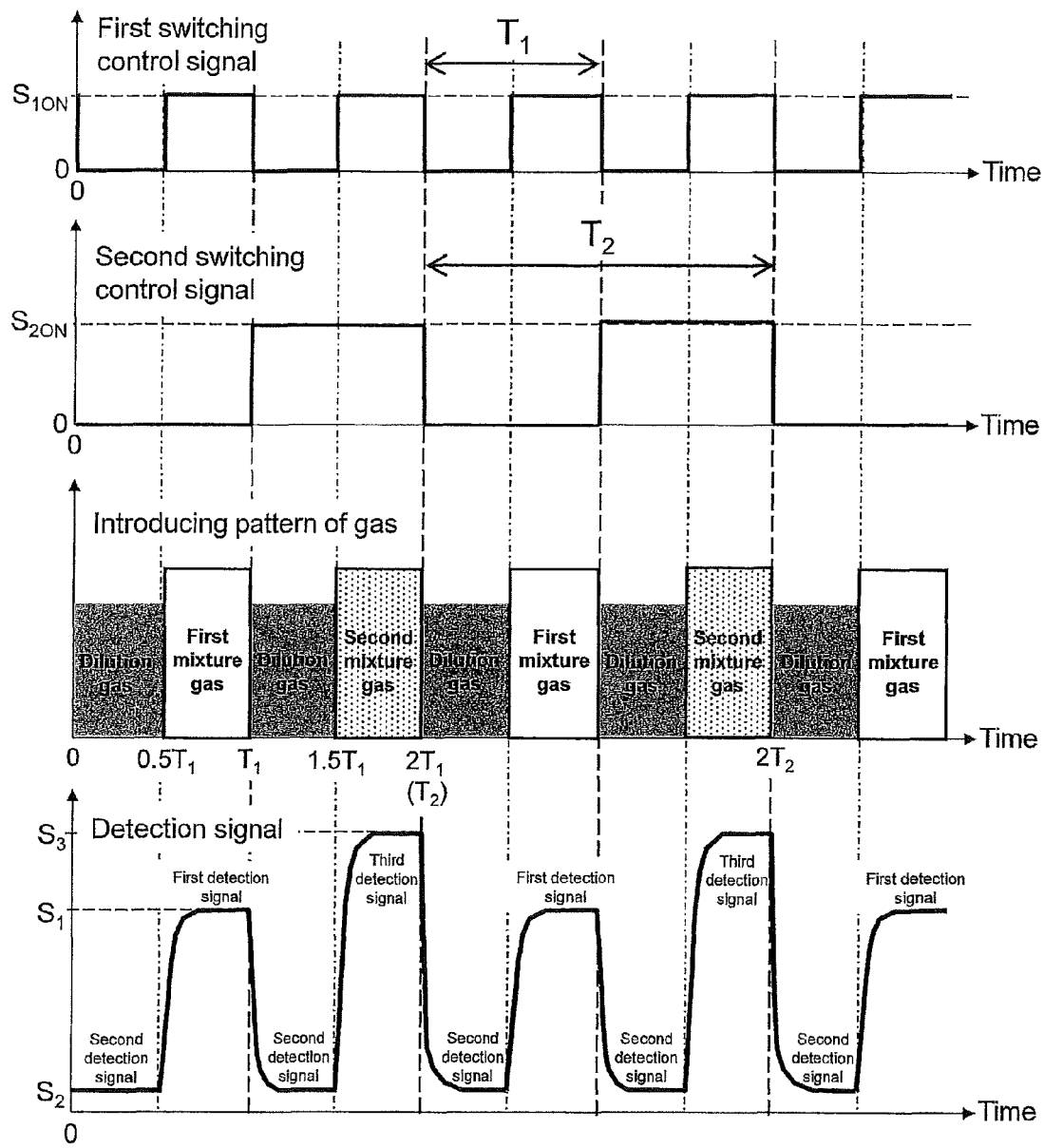

GAS ANALYZING APPARATUS

CROSS-REFERENCE TO RELATED APPLICATIONS

This application claims priority to Japanese Patent Application No. 2013-273411 filed on Dec. 27, 2013, the disclosure of which is hereby incorporated by reference in its entirety.

TECHNICAL FIELD

The present invention relates to a gas analyzing apparatus using a chemical luminescence analyzing method.

BACKGROUND

Conventionally, a gas analyzing apparatus configured to measure a concentration of a component in an exhaust gas generated from a flue, etc. using a chemical luminescence analysis (CLA) method has been known.

For example, Japanese Patent Application Publication No. H7-301603 discloses a CLA type nitric oxide measurement apparatus comprising a pump, a flow controller, a flowmeter, an ozone generator, a smoothing device, and an ozone flow path configured both to supply ozone and to supply a dilution air into a reaction chamber. In this gas analyzing apparatus, a flow rate of the ozone flow path is adjusted appropriately to dilute a luminescence interfering gas such as $CO_2$, etc. and a concentration of ozone is optimized to maximize detection sensitivity of chemical luminescence in accordance with a concentration of nitric oxide in the sample gas. In addition, in this gas analyzing apparatus, a high voltage power source configured to drive the ozone generator is controlled by a pulse-width-modulation type concentration setting unit. Furthermore, in the CLA type nitric oxide measurement apparatus disclosed in Japanese Patent Application Publication No. H7-301603, a section where a concentration of ozone is set to zero is introduced when generating ozone intermittently and a measurement system (a light detector and its amplification system) for measuring intensity of chemical luminescence is calibrated in the section where the concentration of ozone is zero. Thus, high sensitivity amplification can be achieved.

However, a gas analyzing apparatus using CLA method using an ozone generator configured to generate ozone ($O_3$) by electric discharge cannot measure, with high accuracy, a concentration of a predetermined component to be measured in the sample gas, especially when the concentration of the predetermined component is low, such as a concentration of a few parts per million (ppm).

SUMMARY

Various embodiments according to the present disclosure measure the concentration of a predetermined component in the sample gas with high accuracy using CLA method.

A plurality of aspects is explained below as technical solutions. These aspects can be combined arbitrarily as needed.

A gas analyzing apparatus according to one aspect of the present invention is a gas analyzing apparatus configured to measure a concentration of a component gas in a sample gas using CLA method. The gas analyzing apparatus comprises a gas analyzing unit, a luminescence inducing component generating unit, and a measurement signal calculating unit.

The sample gas and/or a standard gas and a luminescence inducing gas are introduced into the gas analyzing unit. The luminescence inducing gas is a gas including a luminescence inducing component. The luminescence inducing component is a component interacting with the component gas. The gas analyzing apparatus is configured to output a detection signal based on an intensity of a reaction light generated by the above interaction.

The luminescence inducing component generating unit is configured to generate the luminescence inducing gas by electric discharge. The electric discharge is generated repeatedly at a discharge interval. The discharge interval is determined based on the concentration of the component gas. The luminescence inducing component generating unit is configured to introduce the generated luminescence inducing gas into the gas analyzing unit.

The measurement signal calculating unit is configured to calculate a first measurement signal based on a first detection signal and a second detection signal. The first measurement signal is for measuring the concentration of the component gas. The first detection signal is a detection signal outputted when the sample gas and the luminescence inducing gas are introduced into the gas analyzing unit. The second detection signal is a detection signal outputted when the standard gas and the luminescence inducing gas are introduced into the gas analyzing unit.

In this gas analyzing apparatus, the luminescence inducing component generating unit first generates the luminescence inducing gas which includes the luminescence inducing component by generating electric discharge repeatedly at the discharge interval. The generated luminescence inducing gas is introduced into the gas analyzing unit.

Next, the standard gas and/or the sample gas are introduced into the gas analyzing unit while the luminescence inducing gas is introduced into the gas analyzing unit. Then, when the standard gas is introduced into the gas analyzing unit, the second detection signal, which is based on the intensity of the reaction light generated by introducing the standard gas and the luminescence inducing component into the gas analyzing unit, is outputted from the gas analyzing unit.

On the other hand, when the sample gas is introduced into the gas analyzing unit, the first detection signal, which is based on the intensity of the reaction light generated by introducing the sample gas and the luminescence inducing component into the gas analyzing unit, is outputted from the gas analyzing unit.

After obtaining the first detection signal and the second detection signal, the measurement signal calculating unit calculates the first measurement signal based on the first detection signal and the second detection signal.

According to this gas analyzing apparatus, the discharge interval used in the luminescence inducing component generating unit is determined based on the concentration of the component gas in the sample gas. Thus, an amount of secondary products included in the luminescence inducing gas can be adjusted based on the concentration of the component gas. Consequently, an influence on the reaction light due to the secondary products can be adjusted in accordance with the concentration of the component gas. As a result, the concentration of the component gas can be measured with high accuracy using the first detection signal.

In addition, according to this gas analyzing apparatus, the measurement signal calculating unit calculates the first measurement signal based on the first detection signal and the second detection signal. In obtaining the second detection signal, a non-zero signal could be generated even when only the standard gas and the luminescence inducing gas are introduced. The first detection signal could also include a signal component generated when the standard gas and the luminescence inducing gas are introduced.

In such a situation, the measurement signal calculating unit can remove the above signal component from the first detection signal when calculating the first measurement signal. As a result, the gas analyzing apparatus can measure the concentration of the component gas with high accuracy using the first measurement signal.

It is acceptable that the discharge interval is set based on a range of a measurable concentration for measuring the concentration of the component gas. In addition, it is acceptable that the discharge interval set when the range of the measurable concentration is the range of the concentration equal to or lower than the predetermined concentration is larger than that when the range of the measurable concentration is the range of the concentration more than the predetermined concentration.

Thus, the generation of the secondary products from the luminescence inducing component generating unit can be reduced especially when the concentration of the component gas in the sample gas is low. As a result, the influence on the reaction light due to the secondary products can be reduced.

It is acceptable that the gas analyzing apparatus further comprises a conversion unit. The conversion unit is configured to generate a converted sample gas from the sample gas. The converted sample gas is a gas further including a converted luminescence component. The converted luminescence component is a component which emits light when interacting with the luminescence inducing component. In this situation, when the converted sample gas and the luminescence inducing gas are introduced into the gas analyzing unit, the gas analyzing unit outputs a third detection signal.

In addition, it is acceptable that the measurement signal calculating unit is configured to calculate a second measurement signal for measuring a concentration of the converted luminescence component, based on the third detection signal and the second detection signal.

Thus, the concentration of a component, which is included in the sample gas and does not cause any interactions with the luminescence inducing component that emits light, can be measured based on the second measurement signal.

It is acceptable that the standard gas and, the sample gas or the converted sample gas, are alternately introduced into the gas analyzing unit in a first period. Thus, the second detection signal and, the first detection signal or the third detection signal, can be obtained in a short period of time. As a result, the concentration of the component gas or the converted luminescence component can be measured with high accuracy.

It is acceptable that the sample gas and the converted sample gas are alternately introduced into the gas analyzing unit in a second period. Thus, the first detection signal and the third detection signal can be obtained in a short period of time. As a result, the concentrations of the component gas and/or the converted luminescence component can be measured with high accuracy.

It is acceptable that, when the sample gas or the converted sample gas are introduced into the gas analyzing unit, a first mixture gas or a second mixture gas is introduced into the gas analyzing unit. The first mixture gas is a mixture of the sample gas and a dilution gas. The second mixture gas is a mixture of the converted sample gas and the dilution gas.

Thus, a component, which interferes with luminescence caused by the interactions between the luminescence inducing component and, the component gas and/or the converted luminescence component, can be diluted.

It is acceptable that the discharge interval is set based on a measured concentration of the component gas. In addition, it is acceptable that the discharge interval set when the measured concentration is equal to or lower than the predetermined concentration is larger than that when the measured concentration is more than the predetermined concentration.

Thus, the generation of the secondary products from the luminescence inducing component generating unit can be reduced especially when the concentration of the component gas in the sample gas is low. As a result, the influence on the reaction light due to the secondary products can be reduced.

As described above, the gas analyzing apparatus of the present invention can measure the concentration of the component gas (and the concentration of the component converted to the converted luminescence component) with high accuracy by using CLA method.

BRIEF DESCRIPTION OF THE DRAWINGS

FIG. 7 is a drawing showing the signal waveforms of a first switching control signal and a second switching control signal, the introduction pattern of gases to a reaction unit, and the signal waveform of a detection signal.

Figure 1:
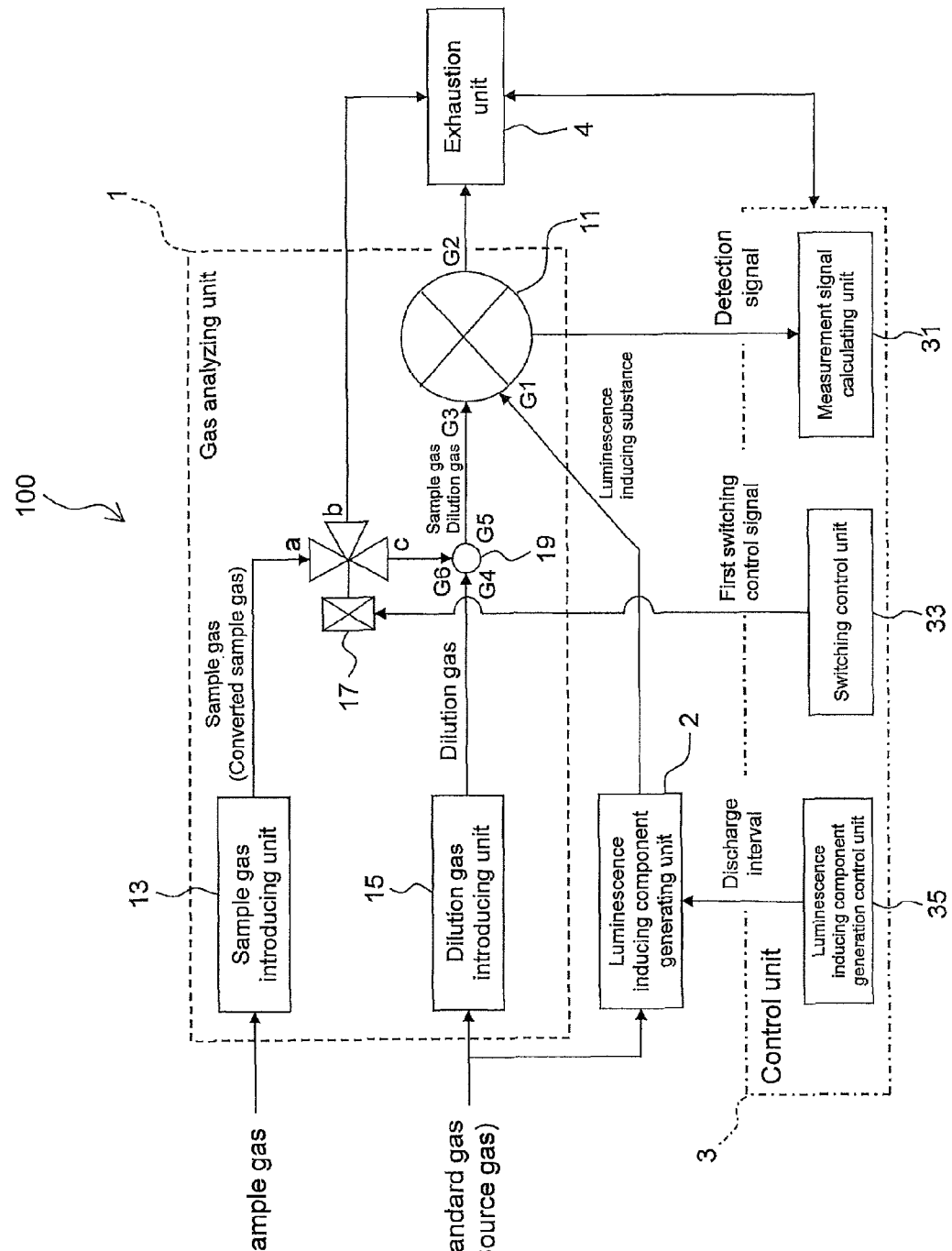
FIG. 1 is a drawing showing the overall configuration of a gas analyzing apparatus.

DETAILED DESCRIPTION (1) First Embodiment
1. Overall Configuration of a Gas Analyzing Apparatus
Referring to FIG. 1, an overall configuration of a gas analyzing apparatus 100 in the present embodiment is explained. FIG. 1 shows the overall configuration of the gas analyzing apparatus. The gas analyzing apparatus 100 shown in FIG. 1 is an apparatus configured to measure a concentration of a component gas in a sample gas using CLA method.

The gas analyzing apparatus 100 comprises a gas analyzing unit 1, a luminescence inducing component generating unit 2, a control unit 3, and an exhaustion unit 4.

The gas analyzing unit 1 is connected to the exhaustion unit 4 such that a gas can be exhausted from the gas analyzing unit 1 by the exhaustion unit 4. The gas analyzing unit 1 is also connected to an outlet side of the luminescence inducing component generating unit 2 such that a gas can be introduced into the gas analyzing unit 1 from an outlet side of the luminescence inducing component generating unit 2. With this configuration, a luminescence inducing gas, which is generated by the luminescence inducing component generating unit 2, can be introduced into the gas analyzing unit 1 by suction of the gas analyzing unit 1 by the exhaustion unit 4.

The sample gas and/or a dilution gas can also be introduced into the gas analyzing unit 1 by suction of the gas analyzing unit 1 by the exhaustion unit 4.

Here, the sample gas and the dilution gas in the present embodiment is explained. The sample gas is a gas containing a nitrogen compound, such as nitrogen oxides ($NO_x$), etc. A gas flowing in flue or a gas generated during any kind of process can be candidates for the sample gas mentioned above.

The dilution gas mainly plays a role in diluting a component (carbon dioxide ($CO_2$), for example) which interferes with the generation of a reaction light generated by the interaction between a luminous component (the component gas) in the sample gas and a luminescence inducing component in the luminescence inducing gas, when the sample gas and the luminescence inducing gas are introduced into the gas analyzing unit 1. Therefore, the dilution gas is introduced together with the sample gas when the sample gas is introduced into the gas analyzing unit 1.

For the reason mentioned above, a gas, which does not contain the component gas to be measured and the component interfering with the generation of the reaction light, can be used as the dilution gas. In the present embodiment, a gas, which is produced by removing the component gas to be measured and the component (carbon dioxide ($CO_2$)) interfering with the generation of the reaction light from the sample gas, is used as the dilution gas. For example, the component gas to be measured (nitrogen oxides ($NO_x$), for example) and the component (carbon dioxide ($CO_2$)) interfering with the generation of the reaction light can be removed by using an absorbing agent (zeolite, etc.) and/or an absorbent (soda lime, etc.). Alternatively, a dry air or a nitrogen ($N_2$) gas can be used as the dilution gas.

On the other hand, a standard gas is introduced into a reaction unit 11 together with the luminescence inducing gas when measuring a concentration of the component gas in the gas analyzing apparatus 100. Then, a detection signal (a second detection signal), which is outputted from the reaction unit 11 when the standard gas and the luminescence inducing gas are introduced into the reaction unit 11, is used as a standard signal for the measurement of the concentration of the component gas. In the present embodiment, the standard gas is the same as the dilution gas described above.

The gas analyzing unit 1 can introduce the sample gas and/or the dilution gas (the standard gas) into an inside of the reaction unit 11 of the gas analyzing unit 1 while introducing the luminescence inducing gas into the inside of the reaction unit 11. By introducing the sample gas and/or the dilution gas while introducing the luminescence inducing gas, the luminous component (the component gas) contained in the sample gas and/or the dilution gas and the luminescence inducing component in the luminescence inducing gas interact with each other. Due to the above interaction, the reaction light is generated inside the reaction unit 11.

In addition, the gas analyzing unit 1 further comprises a light detector, which is not shown in the Figures, and receives the reaction light generated inside the reaction unit 11 using the light detector. Thus, the gas analyzing unit 1 can output a signal based on an intensity of the reaction light, received using the light detector, etc., as a detection signal.

The detailed configuration of the gas analyzing unit 1 will be explained later.

The luminescence inducing component generating unit 2 is configured to generate the luminescence inducing gas containing the luminescence inducing component by electric discharge. In the present embodiment, the luminescence inducing component generating unit 2 is configured to generate the luminescence inducing gas containing ozone ($O_3$) as the luminescence inducing component. Therefore, a gas containing oxygen ($O_2$), which is a source gas for generating ozone ($O_3$) as the luminescence inducing component by electric discharge, can be introduced into the luminescence inducing component generating unit 2. In the present embodiment, the dilution gas (the standard gas) is used as the source gas for generating ozone ($O_3$).

The luminescence inducing component generating unit 2 according to the present embodiment has two gas ports. One gas port is configured to introduce the source gas (the same gas as the dilution gas and the standard gas) for generating ozone ($O_3$). On the other hand, another gas port is connected to the exhaustion unit 4 via the reaction unit 11 of the gas analyzing unit 1 such that a gas is exhausted from another gas port to the exhaustion unit 4. Consequently, the luminescence inducing component generating unit 2 can introduce the source gas for generating ozone ($O_3$) to inside by suction of the luminescence inducing component generating unit 2 by the exhaustion unit 4.

The luminescence inducing component generating unit 2 is configured to generate electric discharge inside the luminescence inducing component generating unit 2, while the source gas is introduced into the inside of the luminescence inducing component generating unit 2. Thus, the luminescence inducing component generating unit 2 can generate the luminescence inducing gas containing ozone ($O_3$) as the luminescence inducing component by using oxygen in the source gas as a main raw material.

In addition, as described above, another gas port of the luminescence inducing component generating unit 2 is connected to the reaction unit 11 such that a gas can flow between them, and the reaction unit 11 is connected to the exhaustion unit 4 such that a gas can flow between them. Therefore, the luminescence inducing component generating unit 2 can introduce the luminescence inducing gas containing the luminescence inducing component generated inside the luminescence inducing component generating unit 2 into the reaction unit 11 of the gas analyzing unit 1 by suction of the reaction unit 11 and the luminescence inducing component generating unit 2 by the exhaustion unit 4.

The luminescence inducing component generating unit 2, which is configured to generate ozone (O3) by using the dilution gas (the standard gas) as the source gas, is inexpensive and simple in structure. However, it has the following problems.

Figure 2:
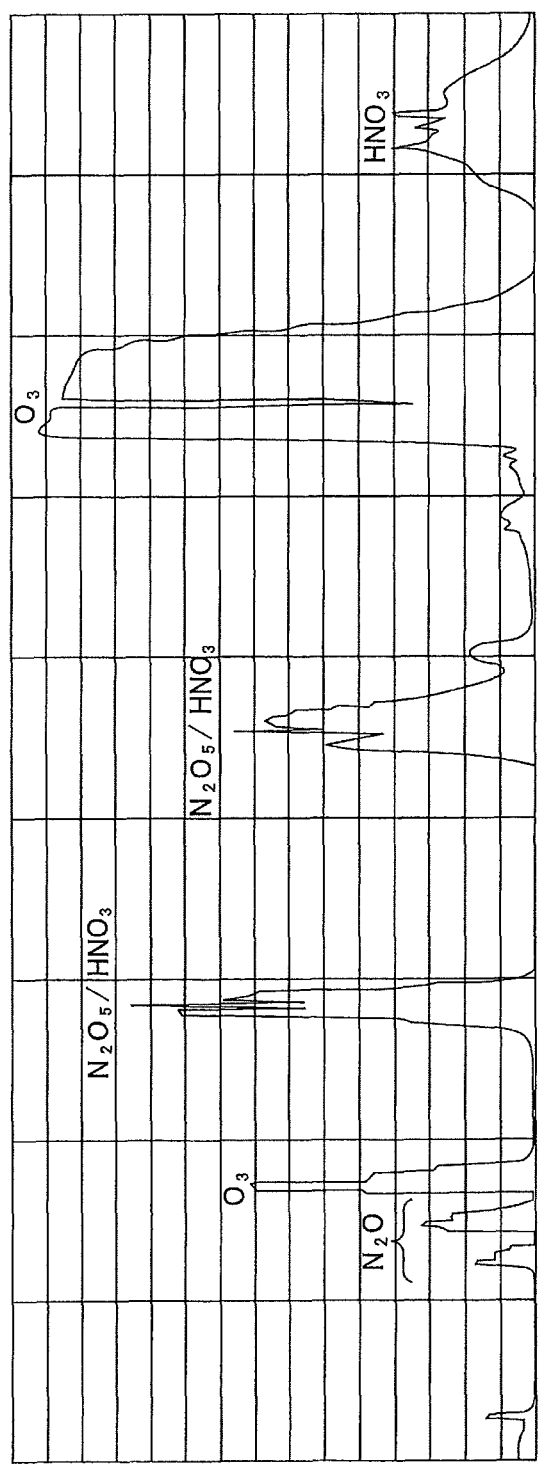
FIG. 2 is a drawing showing the result of the component analysis of a luminescence inducing gas generated by the luminescence

Components (for example, nitrogen compounds) other than oxygen contained in the source gas (the dilution gas or the standard gas) are decomposed or activated as well as oxygen when generating ozone by electric discharge by using the dilution gas (the standard gas) as the source gas. Therefore, as shown in FIG. 2, the luminescence inducing gas generated by the luminescence inducing component generating unit 2 contains nitrogen compounds such as nitrous oxide ($N_2O$), dinitrogen pentoxide ($N_2O_5$), gaseous nitric acid ($HNO_3$), etc., as well as ozone ($O_3$). These components other than ozone are called "secondary products."

The secondary products described above play a role in interfering with the interaction between the luminescence inducing component and the component gas (the luminous component) in the sample gas. For the above reason, when the concentration of the component gas (the luminous component) to be measured in the sample gas is low (on the order of a few ppm.), it is possible that the intensity of the reaction light generated by the interaction between the component gas and the luminescence inducing component becomes weak due to the existence of such secondary products. Consequently, it is possible that the concentration of the component gas is not measured in high accuracy when the concentration of the component gas is calculated from the measurement signal.

In addition, when ozone ($O_3$) is generated by using the dilution gas (the standard gas) as the source gas, it is possible that a component such as nitric monoxide (NO), which interacts with the luminescence inducing component (ozone ($O_3$)) and generates the reaction light, is also generated as the secondary product.

The nitrogen monoxide (NO) as the secondary product described above influences the magnitudes of a first detection signal which is used to measure the concentration of the component gas, and a third detection signal, when the concentration of the component gas is measured by CLA method. In particular, the above influence cannot be ignored when the concentration of the component gas having a few ppm is measured.

Figure 3:
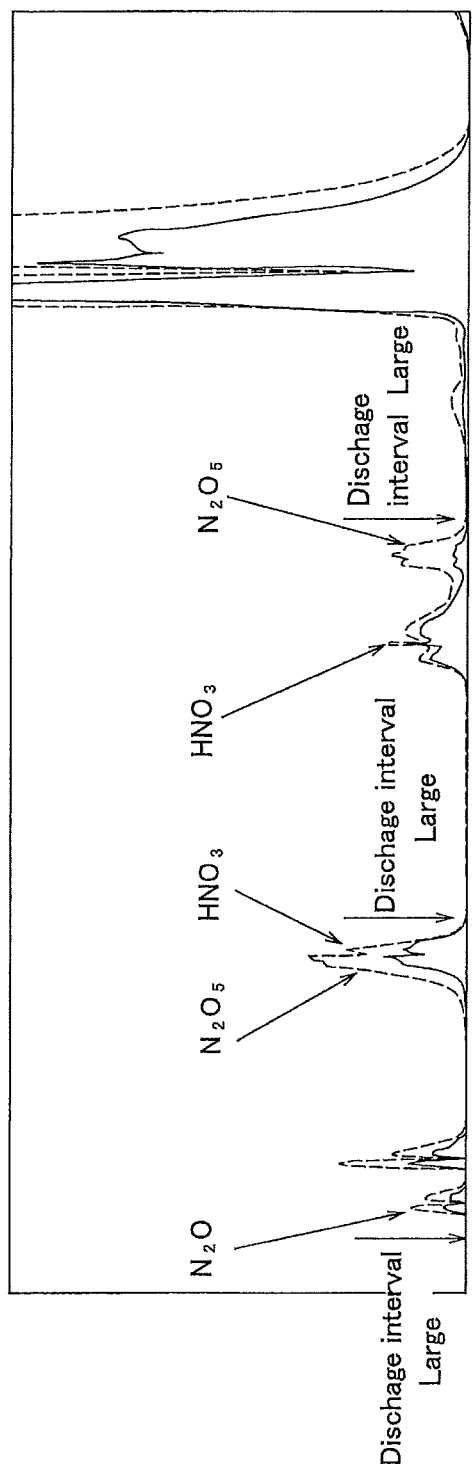
FIG. 3 is a drawing showing the relationship between a discharge interval and an amount of generated secondary products.

To solve the above problem, the luminescence inducing component generating unit 2 is configured to generate electric discharge repeatedly at a discharge interval, which is set (regulated) in advance by a luminescence inducing component generation control unit 35, not constantly. Thus, as shown in FIG. 3, the amount of the above secondary products generated in a predetermined time period can be controlled based on the discharge interval. FIG. 3 shows the relationship between the discharge interval and the amount of generated secondary products.

As discussed later, when the concentration of the component gas in the sample gas is (predicted to be) equal to or less than a predetermined concentration, in other words, when the intensity of the reaction light due to the component gas is predicted to be low, the luminescence inducing component generating unit 2 is configured to adjust the discharge interval based on the concentration of the component gas in the sample gas in order to reduce the generation of the secondary products. More specifically, for example, the discharge interval in the case where the concentration of the component gas in the sample gas is (predicted to be) low (a few ppm in concentration) is set larger than that in the case where the concentration of the component gas in the sample gas is higher (a few hundreds of ppm in concentration).

Thus, minimizing the generation of the secondary products can prevent, to some extent, the interaction between the component gas and the luminescence inducing component from interference with the secondary products, especially when the concentration of the component gas is a few ppm or so. Consequently, even if the concentration of the component gas is low, the intensity of the reaction light can be sufficiently large. As a result, the concentration of the component gas with lower concentrations can be measured with high accuracy.

In addition, the generation of the component such as nitrogen monoxide as the secondary product, which interacts with the luminescence inducing component and emits light, can also be reduced.

On the other hand, by setting the discharge interval smaller than the value used when the concentration of the component gas is low, when the concentration of the component gas is higher (more than 10 ppm, for example), the sufficient amount of ozone ($O_3$) can be supplied to the component gas (the luminous component) in the sample gas. This can prevent, to some extent, the intensity of the reaction light from becoming smaller for the concentration of the component gas.

Thus, by adjusting the discharge interval in accordance with the concentration of the component gas, the gas analyzing apparatus 100 can accurately measure the wider range of the concentration of the component gas.

The control unit 3 is configured to control the units in the gas analyzing apparatus, such as the gas analyzing unit 1, the luminescence inducing component generating unit 2, the exhaustion unit 4, etc. In addition, the control unit 3 is configured to input a detection signal generated based on the intensity of the reaction light generated in the reaction unit 11. Moreover, the control unit 3 is configured to calculate a measurement signal based on the inputted detection signal in order to calculate the concentration of the component gas in the sample gas.

For example, the control unit 3 is a microcomputer system or a computer, which comprises a central processing unit (CPU), a storage device such as a random access memory (RAM), a read only memory (ROM), a hard disk drive (HDD) and/or a solid state drive (SSD), and/or an interface.

When the control unit 3 is the microcomputer system or the computer, some or all of the units in the control unit 3, which will be explained later, may be realized by a computer program stored in the storage device. Some or all of the units in the control unit 3 may be realized by a custom IC.

The exhaustion unit 4 is a pump (not shown in the figure) configured to generate suction, etc. In addition, as described above, the exhaustion unit 4 is connected to the reaction unit 11 of the gas analyzing unit 1 such that a gas can flow between the reaction unit 11 and the exhaustion unit 4. With this configuration, the exhaustion unit 4 can introduce the sample gas and/or the standard gas and the luminescence inducing gas generated by the luminescence inducing component generating unit 2 into the inside of the reaction unit 11 by pumping the inside of the reaction unit 11 to a negative pressure.

Moreover, as described above, the exhaustion unit 4 is connected to the luminescence inducing component generating unit 2 via the reaction unit 11 such that a gas can flow between the luminescence inducing component generating unit 2 and the exhaustion unit 4. Therefore, the exhaustion unit 4 can introduce the source gas (the dilution gas or the standard gas) as a source of the luminescence inducing component into the luminescence inducing component generating unit 2 by pumping the luminescence inducing component generating unit 2, as well as the reaction unit 11, to a negative pressure.

Furthermore, the exhaustion unit 4 has a device (not shown in the figure) configured to decompose the luminescence inducing component (ozone ($O_3$) in the present embodiment). Thus, the exhaustion unit 4 can reduce the amount of the luminescence inducing component exhausted to an outer space.

It should be noted that the amount of the luminescence inducing component generated by the luminescence inducing component generating unit 2 can also be reduced by generating electric discharge repeatedly at the discharge interval. As the result, the amount of the luminescence inducing component exhausted from the exhaustion unit 4 to the outer space can be reduced.

2. Configuration of the Gas Analyzing Unit 2-1. Overall Configuration

Next, the configuration of the gas analyzing unit 1 is explained. The overall configuration of the gas analyzing unit 1 is explained, referring to FIG. 1.

As described above, the gas analyzing unit 1 is configured to output the detection signal based on the reaction light generated by the interaction between the component gas in the sample gas and the luminescence inducing component in the luminescence inducing gas. In addition, the gas analyzing unit 1 according to the present embodiment is configured to introduce alternately the standard gas and a mixture gas (a first mixture gas or a second mixture gas), which is a mixture of the dilution gas and the sample gas (or a converted sample gas) (explained later), into the gas analyzing unit 1 in a first period (cycle) $T_1$.

Therefore, the gas analyzing unit 1 includes the reaction unit 11, a sample gas introducing unit 13, a dilution gas introducing unit 15, a first gas switching unit 17, and a gas converging unit 19.

The reaction unit 11 has at least three gas ports (a first gas port G1, a second gas port G2, and a third gas port G3). The first gas port G1 is connected to one of gas ports of the luminescence inducing component generating unit 2 such that a gas can be flown between the first gas port G1 and the luminescence inducing component generating unit 2. In addition, the second gas port G2 is connected to the exhaustion unit 4 such that a gas can be flown between the second gas port G2 and the exhaustion unit 4.

Therefore, the reaction unit 11 can introduce the luminescence inducing gas inside the reaction unit 11 by suction of the reaction unit 11 by the exhaustion unit 4.

Moreover, the third gas port G3 is connected to the sample gas introducing unit 13 via the gas converging unit 19 and the first gas switching unit 17 such that a gas can flow between the third gas port G3 and the sample gas introducing unit 13. The third gas port G3 is also connected to the dilution gas introducing unit 15 via the gas converging unit 19 such that a gas can flow between the third gas port G3 and the dilution gas introducing unit 15. Therefore, the reaction unit 11 can introduce the standard gas or the mixture gas described above inside the reaction unit 11 while the luminescence inducing gas is introduced into the reaction unit 11, by suction of the reaction unit 11 by the exhaustion unit 4.

Thus, inside the reaction unit 11, the reaction light is generated by the interaction between the luminous component (the component gas and/or a converted luminous component (explained later)) in the sample gas (or the converted sample gas) and the luminescence inducing component in the luminescence inducing gas.

As described above, the mixture gas of the sample gas (the converted sample gas) and the dilution gas is introduced into the reaction unit 11 when the sample gas or the converted sample gas is introduced into the reaction unit 11. By introducing the dilution gas and the sample gas (the converted sample gas) together, the component (carbon dioxide ($CO_2$), etc.), which is contained in the sample gas (the converted sample gas) and interferes with the generation of the reaction light, can be diluted. Consequently, the reaction light based on the concentration of the luminous component in the sample gas can be generated.

In addition, the reaction unit 11 has a light detector, which is not shown in the figure. The reaction light described above is received by the light detector. Consequently, the light detector of the reaction unit 11 can output the detection signal based on the intensity of the reaction light.

Figure 4:
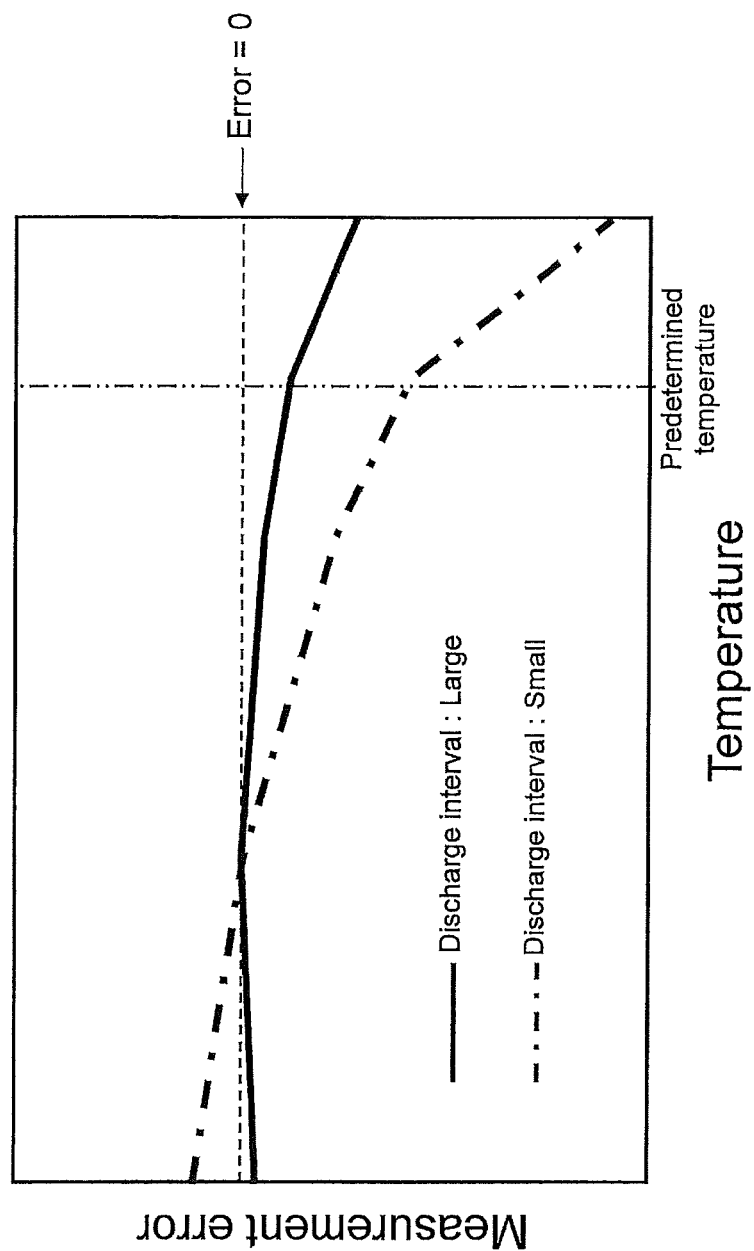
FIG. 4 is a drawing showing the relationship between a temperature around a reaction unit and a measurement error.

Moreover, the temperature of the reaction unit 11 (and around the reaction unit 11) is maintained equal to or less than the predetermined temperature. For example, as shown in FIG. 4, the difference between the measured concentration of the component gas (and/or the converted luminous component) and an actual concentration increases as the temperature increases, when the concentration of nitrogen monoxide (NO) with low concentration (a few ppm or so) is measured. Especially, the measurement error becomes notably large when the temperature around the reaction unit 11 is equal to or higher than the predetermined temperature. FIG. 4 shows the relationship between a temperature around a reaction unit and a measurement error.

The reason why the measurement error increases when the temperature becomes equal to or higher than the predetermined temperature is because the generation of the secondary products described above notably increases when the temperature becomes equal to or higher than the predetermined temperature.

In addition, as shown in FIG. 4, the larger the discharge interval is, the smaller the change of the measurement error to the temperature of the reaction unit 11 (and around the reaction unit 11) becomes.

For the reason above, the change of the measurement value to the temperature can be reduced by maintaining the temperature of the reaction unit 11 (around the reaction unit 11) lower than the predetermined temperature. As the result, the concentration of the component gas (and/or the converted luminous component) can be measured in high accuracy.

Moreover, by increasing the discharge interval of the luminescence inducing component generating unit 2, the occurrence of the measurement error due to the temperature can be inhibited.

The sample gas introducing unit 13 is, for example, a gas flow controller having a gas inlet and a gas outlet. The gas inlet of the sample gas introducing unit 13 is connected to a sampling probe (not shown in the figure) which is arranged at the place where the sample gas is sampled, such that a gas can be transferred between the gas inlet and the sampling probe. On the other hand, the gas outlet of the sample gas introducing unit 13 is connected to the gas port a of the first gas switching unit 17 such that a gas can flow between the gas outlet and the gas port a. The gas outlet of the sample gas introducing unit 13 is connected to the exhaustion unit 4 via the first gas switching unit 17, the gas converging unit 19, and the reaction unit 11 such that a gas can flow between the gas outlet and the exhaustion unit 4.

Thus, the sample gas introducing unit 13 can flow the sample gas which is sampled by the sampling probe to the gas port a of the first gas switching unit 17 by suction by the exhaustion unit 4, while the flow rate is adjusted appropriately.

In addition, the sample gas introducing unit 13 has a conversion unit 131 (explained later), which is configured to convert, out of the components in the sample gas, a component which does not interact with the luminescence inducing component or a component which interacts with the luminescence inducing component but does not emit light (generally, these are the components other than the component gas), to the converted luminous component which emits light by interacting with the luminescence inducing component. The sample gas introducing unit 13 is configured to exhaust the sample gas or the converted sample gas containing the converted luminous component.

Thus, the concentration of the component, which is contained in the sample gas and does not interact with the luminescence inducing component and emit light, can be measured. The detailed configuration of the sample gas introducing unit 13 will be explained later.

The dilution gas introducing unit 15 is, for example, a gas flow controller having a gas inlet and a gas outlet. The gas outlet of the dilution gas introducing unit 15 is connected to the sampling probe (not shown in the figure) via a column which is filled with the absorbent (soda lime, etc.) and/or the absorbing agent (zeolite, etc.) described above such that a gas can be flown between the gas outlet of the dilution gas introducing unit 15 and the sampling probe. As the result, the dilution gas introducing unit 15 can generate the dilution gas and the standard gas by removing the component gas and the components which interfere with the generation of the reaction light, from the sample gas.

In addition, the dilution gas introducing unit 15 is connected to the exhaustion unit 4 via the gas converging unit 19 and the reaction unit 11 such that a gas can flow between the dilution gas introducing unit 15 and the exhaustion unit 4. Thus, the dilution gas introducing unit 15 can flow the dilution gas and the standard gas, which are generated from the sample gas, to the gas converging unit 19 and the reaction unit 11 by suction by the exhaustion unit 4, while the flow rate is adjusted appropriately.

The first gas switching unit 17 is, for example, a three-way solenoid valve having three gas ports a, b, and c. The first gas switching unit 17 is configured to select whether a gas can flow between the gas ports a and b or between the gas ports a and c, based on a first switching control signal (explained later) outputted from a switching control unit 33 (explained later) of the control unit 3. It should be noted that, in the present embodiment, the first gas switching unit 17 enables a gas to flow between the gas ports a and b when the magnitude of the first switching control signal is zero. On the other hand, the first gas switching unit 17 enables a gas to flow between the gas ports a and c when the magnitude of the first switching control signal is $S_{1_{ON}}$ (explained later).

The gas port a of the first gas switching unit 17 is connected to the sample gas introducing unit 13 such that a gas can flow between the gas port a of the first gas switching unit 17 and the sample gas introducing unit 13. In addition, the gas port b of the first gas switching unit 17 is connected to the exhaustion unit 4 such that a gas can flow between the gas port b of the first gas switching unit 17 and the exhaustion unit 4. Furthermore, the gas port c of the first gas switching unit 17 is connected to the gas converging unit 19 such that a gas can flow between the gas port c of the first gas switching unit 17 and the gas converging unit 19.

Thus, the first gas switching unit 17 can flow the sample gas or the converted sample gas, which are introduced to the gas port a, to the exhaustion unit 4, when a gas can flow between the gas ports a and b. In other words, in this case, the sample gas or the converted sample gas is not introduced into the reaction unit.

On the other hand, when a gas can flow between gas ports a and c, the first gas switching unit 17 can flow the sample gas or the converted sample gas to the gas converging unit 19 by suction by the exhaustion unit 4.

The gas converging unit 19 is, for example, a gas piping component (generally, a gas piping component called "tee") having three gas ports (a fourth gas port G4, a fifth gas port G5, and a sixth gas port G6). The fourth gas port G4 is connected to the dilution gas introducing unit 15 such that a gas can flow between the fourth gas port G4 and the dilution gas introducing unit 15. In addition, the fifth gas port G5 is connected to the reaction unit 11 such that a gas can flow between the fifth gas port G5 and the reaction unit 11. Furthermore, the sixth gas port G6 is connected to the gas port c of the first gas switching unit 17 such that a gas can flow between the sixth gas port G6 and the gas port c of the first gas switching unit 17.

Thus, the gas converging unit 19 can exhaust, from the fifth gas port G5, the first mixture gas, which is a mixture of the dilution gas introduced from the fourth gas port G4 and the sample gas introduced from the sixth gas port G6, or the second mixture gas, which is a mixture of the dilution gas and the converted sample gas from the sixth gas port G6, when the sample gas or the converted sample gas is introduced to the sixth gas port G6. Then, the first mixture gas or the second mixture gas exhausted from the fifth gas port G5 is introduced into the reaction unit 11.

On the other hand, when neither the sample gas nor the converted sample gas is introduced to the sixth gas port G6, the gas converging unit 19 can exhaust only the standard gas (the dilution gas) from the fifth gas port G5. Then, the standard gas (the dilution gas) exhausted from the fifth gas port G5 is introduced into the reaction unit 11.

2-2. Configuration of the Sample Gas Introducing Unit

Figure 5:
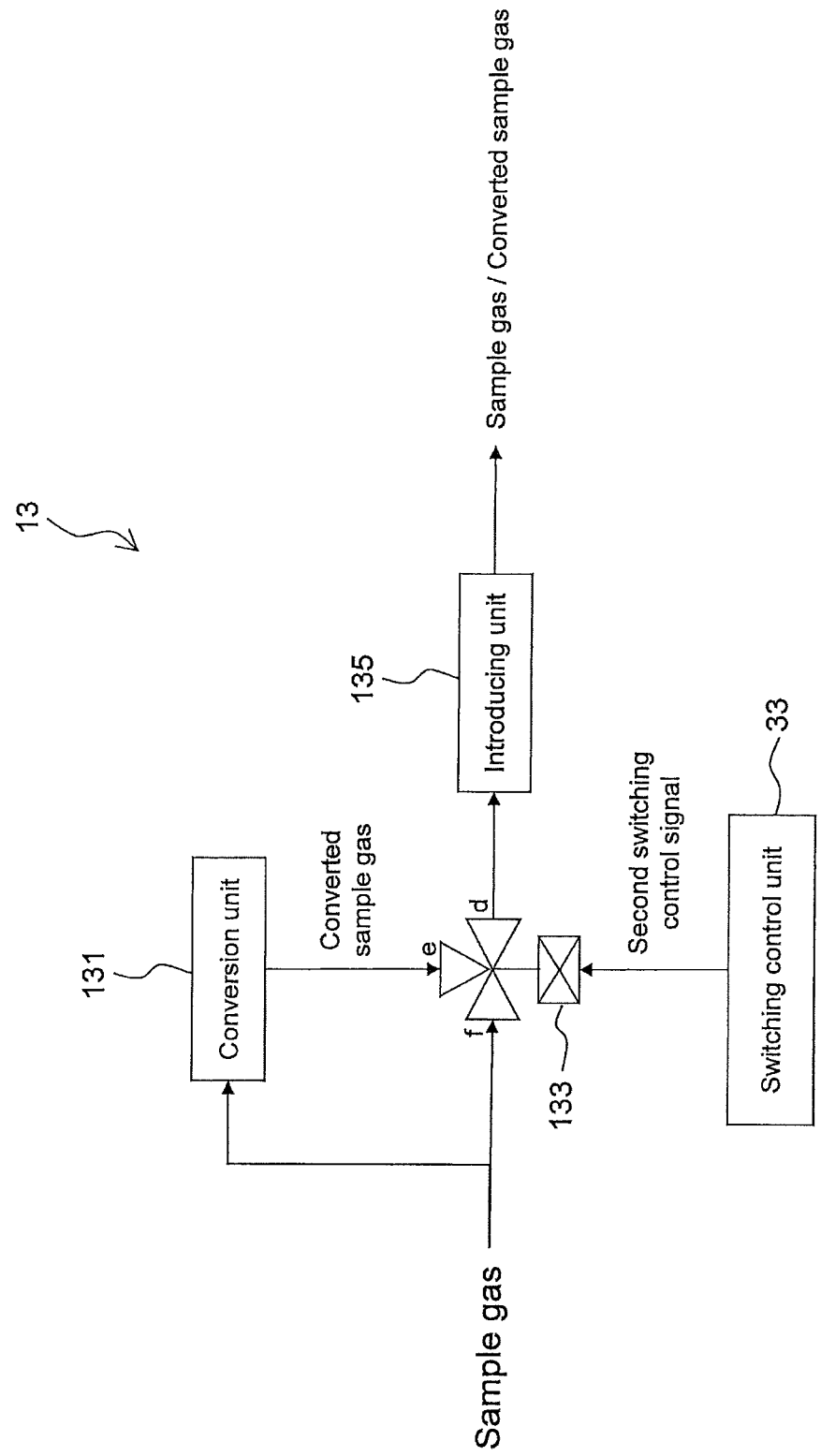
FIG. 5 is a drawing showing the detailed configuration of a sample gas introducing unit.

Next, the detail of the configuration of the sample gas introducing unit 13 is explained, referring to FIG. 5. FIG. 5 shows the detailed structure of the sample gas introducing unit. The sample gas introducing unit 13 shown in FIG. 5 is a sample gas introducing unit configured to introduce not only the sample gas but also the converted sample gas into the reaction unit 11.

The converted sample gas is a gas containing the converted luminous component, which is generated by converting the components (nitrogen dioxide ($NO_2$) and ammonia ($NH_3$), for example) other than component gas (nitrogen monoxide (NO), for example) contained in the sample gas, which does not emit light by interacting with the luminescence inducing component (ozone ($O_3$)), to the component (nitrogen monoxide (NO), for example) which emits light by interacting with the luminescence inducing component.

For the reason described above, the sample gas introducing unit 13 has the conversion unit 131, a second gas switching unit 133, and an introducing unit 135.

The conversion unit 131 has a gas inlet and a gas outlet. The gas inlet of the conversion unit 131 is connected to the sampling probe (not shown in the figure) arranged at the place where the sample gas is sampled such that a gas can flow between the gas inlet of the conversion unit 131 and the sampling probe. In addition, the gas outlet of the conversion unit 131 is connected to a gas port e of the second gas switching unit 133 such that a gas can flow between the gas outlet of the conversion unit 131 and the gas port e of the second gas switching unit 133. Thus, the gas outlet of the conversion unit 131 is connected to the exhaustion unit 4 via the second gas switching unit 133, the introducing unit 135, the first gas switching unit 17, the gas converging unit 19, and the reaction unit 11 such that a gas can be flown between the gas outlet of the conversion unit 131 and the exhaustion unit 4. As the result, the conversion unit 131 can introduce the sample gas from the sampling probe to inside the conversion unit 131 by suction by the exhaustion unit 4.

The conversion unit 131 has a device (a converter) configured to convert the components, which does not interact with the luminescence inducing component and emit light, to the converted luminous component which interacts with the luminescence inducing component and emits light. In other words, the components introduced into the conversion unit 131, which does not interact with the luminescence inducing component and emit light, is converted to the converted luminous component.

The sample gas is converted to the converted sample gas when the sample gas passes through the conversion unit 131. Then, the converted sample gas is exhausted from the gas outlet of the conversion unit 131 to the gas port e of the second gas switching unit 133 by suction by exhaustion unit 4.

With the conversion unit 131 described above, the concentration of the component other than the component gas (the component which interacts with the luminescence inducing component and emits light) in the sample gas can also be measured based on the reaction light generated when the converted sample gas is introduced into the reaction unit 11.

The second gas switching unit 133 is a three-way solenoid valve having three gas ports d, e, and f. The second gas switching unit 133 is connected to the switching control unit 33 (explained later) such that they can communicate with each other. Thus, the second gas switching unit 133 is configured to select, based on a second switching control signal (explained later) outputted from the switching control unit 33, whether a gas can flow between the gas ports d and e or between the gas ports d and f.

The gas port d of the second gas switching unit 133 is connected to the gas inlet of the introducing unit 135 such that a gas can flow between the gas port d of the second gas switching unit 133 and the gas inlet of the introducing unit 135. In addition, the gas port e is connected to the gas outlet of the conversion unit 131 such that a gas can flow between the gas port e and the gas outlet of the conversion unit 131. Furthermore, the gas port f is connected to the sampling probe (not shown in the figure) such that a gas can flow between the gas port f and the sampling probe.

Thus, the second gas switching unit 133 can exhaust the converted sample gas from the gas port d by enabling a gas to flow between the gas ports d and e based on the second switching control signal by suction by the exhaustion unit 4. In addition, the second gas switching unit 133 can exhaust the sample gas sampled by the sampling probe from the gas port d by enabling a gas to flow between the gas ports d and f.

In other words, the second gas switching unit 133 can exhaust either the sample gas or the converted sample gas from the gas port d based on the second switching control signal. It should be noted that, in the present embodiment, the second gas switching unit 133 enables a gas to flow between the gas ports d and f when the magnitude of the second switching control signal is zero. On the other hand, when the magnitude of the second switching control signal is $S_{2ON}$, the second gas switching unit 133 enables a gas to flow between the gas ports d and e.

The introducing unit 135 is, for example, a flow controller having a gas inlet and a gas outlet. The gas inlet of the introducing unit 135 is connected to the gas port d of the second gas switching unit 133 such that a gas can flow between the gas inlet of the introducing unit 135 and the gas port d of the second gas switching unit 133. In addition, the gas outlet of the introducing unit 135 is connected to the exhaustion unit 4 via the first gas switching unit 17, the gas converging unit 19, and the reaction unit 11.

Thus, the introducing unit 135 can exhaust the sample gas or the converted sample gas, which is exhausted from the second gas switching unit 133, from the gas outlet of the introducing unit 135 by the suction by the exhaustion unit 4, while the flow rate is adjusted appropriately.

As described above, with the sample gas introducing unit 13 having the conversion unit 131 and configured to exhaust either the sample gas or the converted sample gas exhausted from the conversion unit 131, either the sample gas containing the component gas or the converted sample gas containing the component gas and the converted luminous component can be introduced into the reaction unit 11.

As a result, not only the concentration of the component gas which interacts with the luminescence inducing component and emits light, but also the concentration of the component which is present in the sample gas and converted to the converted luminous component, can be calculated based on the reaction light generated in the reaction unit 11.

3. Configuration of the Control Unit

Next, the configuration of the control unit 3 is explained, referring to FIG. 1. The control unit 3 includes a measurement signal calculating unit 31, the switching control unit 33, and a luminescence inducing component generation control unit 35.

The measurement signal calculating unit 31 is connected to the reaction unit 11 of the gas analyzing unit 1 such that the measurement signal calculating unit 31 and the reaction unit 11 can communicate with each other. Thus, the measurement signal calculating unit 31 can input the detection signal.

In the present embodiment, the detection signal includes a first detection signal, a second detection signal, and a third detection signal. The first detection signal is a detection signal outputted from the light detector based on the reaction light generated when the first mixture gas, which is the mixture gas of the sample gas and the dilution gas, and the luminescence inducing gas are introduced into the reaction unit 11. The second detection signal is a detection signal based on the reaction light generated when the standard gas (same as the dilution gas) and the luminescence inducing gas are introduced into the reaction unit 11. The third detection signal is a detection signal based on the reaction light generated when the second mixture gas, which is the mixture gas of the converted sample gas and the dilution gas, and the luminescence inducing gas are introduced into the reaction unit 11.

Therefore, the second detection signal is used as the baseline of a first measurement signal and a second measurement signal for measuring the concentrations of the component gas and/or the converted luminous component in the sample gas. This is because the second detection signal is the detection signal obtained when only the standard gas is introduced into the reaction unit 11. In addition, this is because the component contained in the standard gas is the same as that contained in the sample gas except for the removed component gas and the components which interferes with the generation of the reaction light.

Therefore, the measurement signal calculating unit 31 is configured to calculate the first measurement signal for measuring the concentration of the component gas in the sample gas, based on the first detection signal and the second detection signal. More specifically, the measurement signal calculating unit 31 is configured to calculate the first measurement signal based on the difference between the first detection signal and the second detection signal. Thus, the measurement signal calculating unit 31 can subtract a signal component, generated when the standard gas (same as the dilution gas) and the luminescence inducing gas (luminescence inducing component) are introduced into the reaction unit 11, from the first detection signal.

In addition, the measurement signal calculating unit 31 is configured to calculate the second measurement signal for measuring the concentration of the converted luminous component in the converted sample gas, based on the third detection signal and the second detection signal. More specifically, the measurement signal calculating unit 31 is configured to calculate the second measurement signal based on the difference between the third detection signal and the second detection signal.

Thus, the second measurement signal can be calculated by subtracting a signal component other than signal components due to the component gas and the converted luminous component, from the third detection signal. It should be noted that the concentration of only the converted luminous component (the component converted to the converted luminous component by the conversion unit 131) can be calculated based on the measurement signal calculated by subtracting the first measurement signal from the second measurement signal.

The switching control unit 33 is connected to the first gas switching unit 17 such that the switching control unit 33 and the first gas switching unit 17 can communicate with each other. Thus, the switching control unit 33 can output the first switching control signal to the first gas switching unit 17. As the result, the first gas switching unit 17 can select whether a gas can flow between the gas ports a and b of the first gas switching unit 17 or between the gas ports a and c, based on the first switching control signal.

In addition, the switching control unit 33 is connected to the second gas switching unit 133 such that the switching control unit 33 and the second gas switching unit 133 can communicate with each other. Thus, the switching control unit 33 can output the second switching control signal to the second gas switching unit 133. As the result, the second gas switching unit 133 can select whether a gas can flow between the gas ports d and e of the second gas switching unit 133 or between the gas ports d and f, based on the second switching control signal.

For example, a square wave signal which has a first period $T_1$ and can drive the first gas switching unit 17 as the solenoid valve (having the signal amplitude $S_{1ON}$) can be used as the first switching control signal outputted from the switching control unit 33. In addition, for example, a square wave signal which has a second period (cycle) $T_2$ and can drive the second gas switching unit 133 as the solenoid valve (having the signal amplitude $S_{2ON}$) can be used as the second switching control signal.

The luminescence inducing component generation control unit 35 is connected to the luminescence inducing component generating unit 2 such that the luminescence inducing component generation control unit 35 and the luminescence inducing component generating unit 2 can communicate with each other. Thus, the luminescence inducing component generation control unit 35 can output a signal which controls the discharge interval to the luminescence inducing component generating unit 2. As the result, the luminescence inducing component generating unit 2 can control the discharge interval at which electric discharge is generated repeatedly, as instructed by the luminescence inducing component generation control unit 35.

4. Operation of the Gas Analyzing Apparatus

Figure 6A:
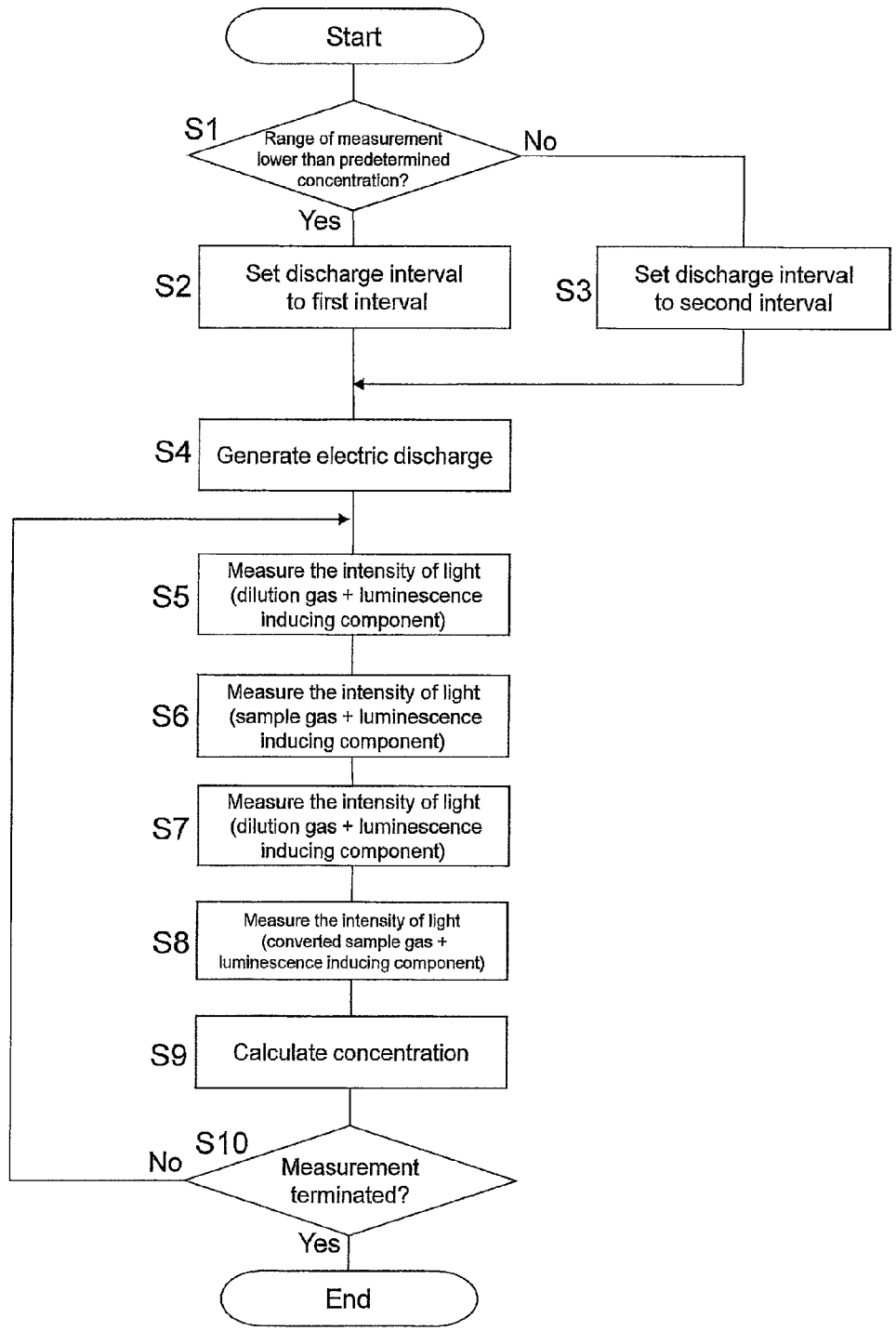
FIG. 6A is a flowchart showing the basic operation of a gas analyzing apparatus.
Figure 6B:
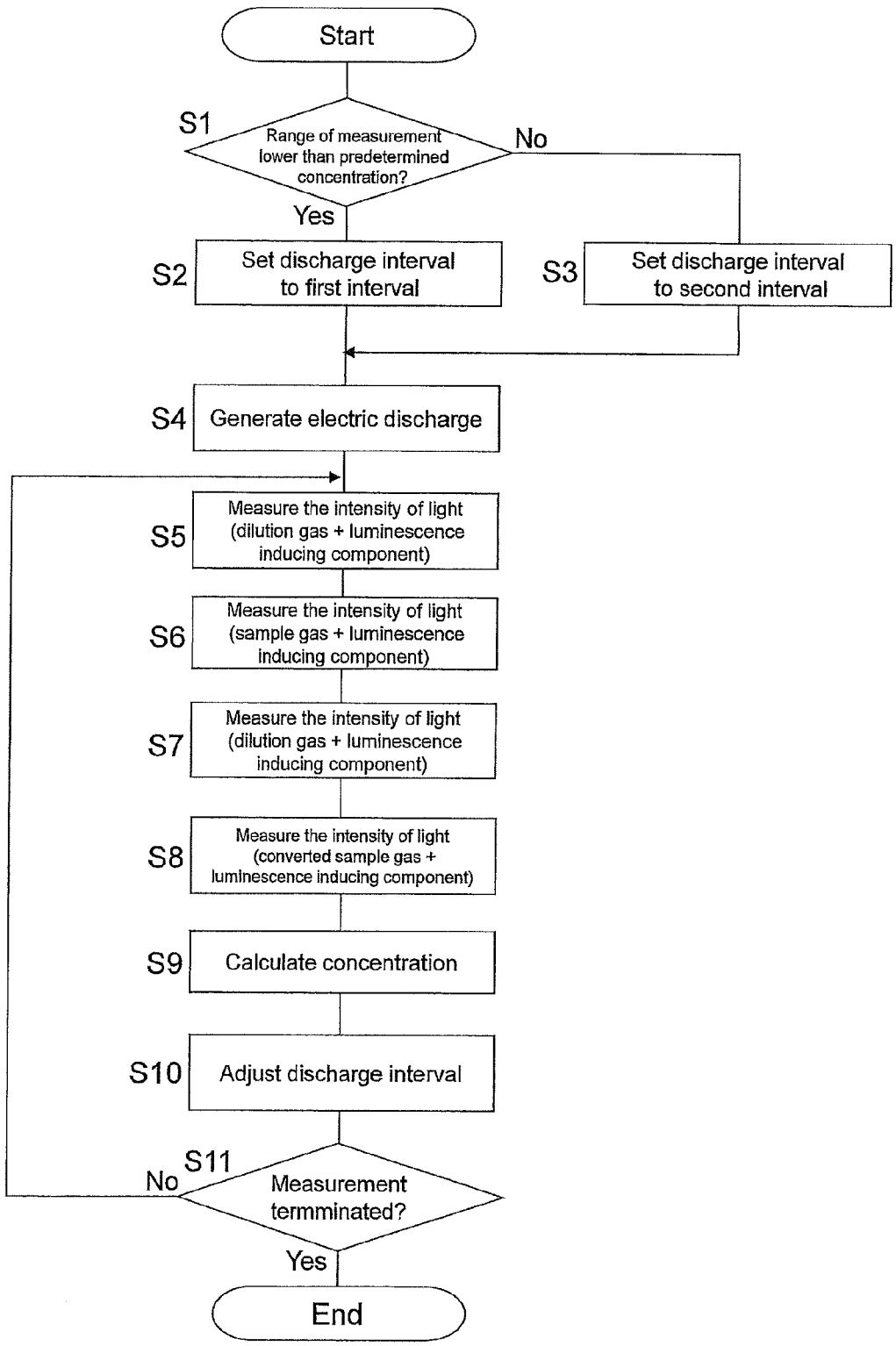
FIG. 6B is a flowchart showing the operation of a gas analyzing apparatus when a discharge interval is adjusted after the measurement of the concentration of a component gas.

Next, the operation of the gas analyzing apparatus 100 according to the present embodiment is explained, referring to FIGS. 6A and 6B. FIG. 6A is a flowchart showing a basic operation of the gas analyzing apparatus. FIG. 6B is a flowchart showing the operation of the gas analyzing apparatus when adjusting the discharge interval after measuring the concentration of the component gas. It should be noted that, in the present embodiment, it is assumed that the second period $T_2$ of the second switching control signal is twice as large as the first period $T_1$ of the first switching control signal. It is also assumed that the rise or decay of the second switching control signal is synchronized with the decay of the first switching control signal.

At the timing when the gas analyzing apparatus 100 starts its operation, the exhaustion unit 4 starts operating. Thus, the pressure inside the reaction unit 11 becomes a negative pressure and therefore the dilution gas (the standard gas), the sample gas and/or the converted sample gas, and the luminescence inducing gas can be introduced into the reaction unit 11.

In addition, at the timing when the gas analyzing apparatus 100 starts its operation, the switching control unit 33 in its initial state outputs the first switching control signal with a zero value. Thus, the first gas switching unit 17 in its initial state enables a gas to flow between the gas ports a and b. Therefore, in the initial state, the dilution gas (the standard gas) is introduced into the reaction unit 11.

After the gas analyzing apparatus 100 starts its operation and before measuring the concentration of the component gas in the sample gas, the control unit 3 sets the range of the measurable concentration of the gas analyzing apparatus 100 (step S1). If the range of the measurable concentration is the range of the concentration equal to or lower than the predetermined concentration (if "Yes" in step S1), the luminescence inducing component generation control unit 35 sets (regulates) the discharge interval to a first interval (step S2).

On the other hand, if the range of the measurable concentration is the range of the concentration higher than the predetermined concentration (if "No" in step S1), the luminescence inducing component generation control unit 35 sets the discharge interval to a second interval which is smaller than the first interval (step S3).

By setting the discharge interval to the first interval (larger interval), when the range of the measurable concentration of the gas analyzing apparatus 100 is set to the range of the concentration equal to or lower than the predetermined concentration in order to measure the concentration of the sample gas with lower concentrations, the generation of the secondary products by the luminescence inducing component generating unit 2 can be reduced.

This can prevent, to some extent, the secondary products from interfering with the interaction between the component gas (and/or the converted luminous component) and the luminescence inducing component. As a result, the sufficient intensity of the reaction light can be obtained even if the concentration of the component gas (and/or the converted luminous component) is low (a few ppm in concentration).

On the other hand, by setting the discharge interval to the second interval (smaller interval), when the concentration of the component gas is higher than the predetermined concentration, the sufficient amount of ozone ($O_3$) (the luminescence inducing component) can be supplied to the component gas (and/or the converted luminous component). This can prevent the intensity of the reaction light from becoming smaller for the concentration of the component gas (and/or the converted luminous component).

After setting the discharge interval, the luminescence inducing component generating unit 2 generates electric discharge repeatedly at the discharge interval set in advance (step S4). Thus, the luminescence inducing component generating unit 2 generates ozone ($O_3$) as the luminescence inducing component (and the secondary products described above) by using the dilution gas (the standard gas) introduced inside the luminescence inducing component generating unit 2 as the source material.

After the luminescence inducing component generating unit 2 starts generating electric discharge, the switching control unit 33 generates the first switching control signal with the square waveform having the first period $T_1$ and the second switching control signal with the square waveform having the second period $T_2$. Here, the explanation described below will be made, referring to FIG. 7, assuming that time is set to zero at the timing where both the first switching control signal and the second switching control signal are zero. FIG. 7 shows the waveforms of the first switching control signal and the second switching control signal, the introduction pattern of the gas into the reaction unit 11, and the signal waveform of the detection signal.

When time t is between zero and a half of the first period ($0.5T_1$), the signal value of the first switching control signal is zero. Therefore, in the first gas switching unit 17, a gas can flow between the gas ports a and b. In other words, the sample gas (or the converted sample gas) bypasses the reaction unit 11 and is exhausted to the exhaustion unit 4. As a result, as shown in the introduction pattern of the gas of FIG. 7, the standard gas (the dilution gas) and the luminescence inducing gas are introduced into the reaction unit 11 when time t is between zero and a half of the first period ($0.5T_1$).

At this timing, the measurement signal calculating unit 31 obtains from the reaction unit 11 the second detection signal based on the intensity of the light generated when the standard gas (the dilution gas) and the luminescence inducing gas are introduced into the reaction unit 11 (step S5). Then, the measurement signal calculating unit 31 stores the obtained second detection signal to a storing unit of the control unit 3.

As shown in FIG. 7, the second detection signal obtained at this timing is the signal having the signal value of $S_2$ when the signal is stable. As such, a non-zero signal is generated even when only the standard gas (same as the dilution gas) and the luminescence inducing gas are introduced into the reaction unit 11. The main cause of the generation of such a signal component is nitrogen monoxide, etc. generated as the secondary products by the luminescence inducing component generating unit 2. Even if the generation of the secondary products can be inhibited by setting the discharge interval in the luminescence inducing component generating unit 2 to a large value, the influence of the generation of the reaction light due to nitrogen monoxide as the secondary products cannot be ignored when the concentration of the component gas to be measured is low (a few ppm in concentration).

In such a situation, as explained later, by subtracting the second detection signal from the first detection signal and the third detection signal, the signal component generated due to nitrogen monoxide, etc. as the secondary products contained in the first detection signal and the third detection signal can be subtracted.

Next, when time t is between $0.5T_1$ and the first period $T_1$, the signal value of the first switching control signal is $S_{1ON}$. On the other hand, the signal value of the second switching control signal is still zero.

Therefore, in the second gas switching unit 133, a gas can flow between the gas ports d and f. In other words, the sample gas is exhausted from the sample gas introducing unit 13 (the introducing unit 135). In addition, in the first gas switching unit 17, a gas can flow between the gas ports a and c. In other words, the sample gas is exhausted from the gas port c of the first gas switching unit 17.

Thus, as shown in the introducing pattern of the gas of FIG. 7, the first mixture gas, generated by mixing the dilution gas and the sample gas in the gas converging unit 19, and the luminescence inducing gas are introduced into the reaction unit 11 when time t is between $0.5T_1$ and the first period $T_1$.

At this timing, the measurement signal calculating unit 31 obtains from the reaction unit 11 the first detection signal, based on the intensity of the light generated when the first mixture gas (the dilution gas and the sample gas) and the luminescence inducing gas are introduced into the reaction unit 11 (step S6). Then, the measurement signal calculating unit 31 stores the obtained first detection signal to the storing unit of the control unit 3.

As shown in FIG. 7, the first detection signal obtained at this timing is the signal having the signal value of $S_1$ when the signal is stable.

Furthermore, when time t is between $T_1$ and the three halves of the first period $T_1$ ($1.5T_1$), the signal value of the first switching control signal becomes zero again. Therefore, as shown in the introducing pattern of gas of FIG. 7, the standard gas (the dilution gas) and the luminescence inducing gas are introduced into the reaction unit 11. At this timing, the measurement signal calculating unit 31 again obtains the second detection signal from the reaction unit 11 (step S7). Then, the measurement signal calculating unit 31 stores the obtained second detection signal to the storing unit of the control unit 3.

When time t is between $1.5T_1$ and the end of the second period of the first switching control signal (in other words, $t=2T_1$), the signal value of the first switching control signal becomes $S_{1ON}$ again. On the other hand, the signal value of the second switching control signal becomes $S_{2ON}$.

Therefore, in the second gas switching unit 133, a gas can flow between the gas ports d and e. In other words, the converted sample gas is exhausted from the sample gas introducing unit 13 (the introducing unit 135). In addition, in the first gas switching unit 17, a gas can flow between the gas ports a and c. Therefore, the converted sample gas is exhausted from the gas port c of the first gas switching unit 17.

As a result, as shown in the introducing pattern of gas of FIG. 7, the second mixture gas, generated by mixing the dilution gas and the converted sample gas in the gas converging unit 19, and the luminescence inducing gas are introduced into the reaction unit 11.

At this timing, the measurement signal calculating unit 31 obtains from the reaction unit 11 the third detection signal, based on the intensity of the light generated when the second mixture gas (the dilution gas and the converted sample gas) and the luminescence inducing gas are introduced into the reaction unit 11 (step S8). Then, the measurement signal calculating unit 31 stores the obtained third detection signal to the storing unit of the control unit 3.

As shown in FIG. 7, the third detection signal obtained at this timing is the signal having the signal value of $S_3$ when the signal is stable.

As described above, by generating the introducing pattern of gas as shown in FIG. 7 using the first switching control signal and the second switching control signal, within the period twice as large as the first period $T_1$ between steps S5 and S8, in other words, within the second period $T_2$, the first detection signal, the second detection signal, and the third detection signal can be obtained.

Obtaining the first detection signal, the second detection signal, and the third detection signal in short period of time as described above can minimize the variation of the baseline signal contained in these three signals.

In other words, by using the second detection signal as the baseline signal for the first detection signal and the third detection signal, the signal component based on the light emission generated by the interaction between the component gas and the luminescence inducing component, and the signal component based on the light emission generated by the interaction between the converted luminous component (and the component gas) and the luminescence inducing component can be obtained from the first detection signal and the third detection signal, respectively, in almost just proportion.

In addition, by introducing alternately the standard gas (the dilution gas) and the sample gas or the converted sample gas into the reaction unit 11, the contamination of the reaction unit 11 due to the sample gas or the converted sample gas can be inhibited. As the result, the frequency of the maintenance of the gas analyzing apparatus 100 can be reduced.

After obtaining the first detection signal, the two second detection signals, and the third detection signal by step S8, the measurement signal calculating unit 31 reads out the first detection signal, the second detection signals, and the third detection signal stored in the storing unit and calculates the first measurement signal for measuring the concentration of the component gas and the second measurement gas for measuring the concentration of the converted luminous component (the component in the sample gas converted to the converted luminous component by the conversion unit 131), based on these three detection signals (step S9).

In the present embodiment, the measurement signal calculating unit 31 calculates the first measurement signal based on the difference between the signal value $S_1$ when the first detection signal is stable and the signal value $S_2$ when the second detection signal is stable. On the other hand, the measurement signal calculating unit 31 calculates the second measurement signal based on the difference between the signal value $S_3$ when the third detection signal is stable and the signal value $S_2$ when the second detection signal is stable.

Then, the measurement signal calculating unit 31 calculates the concentration of the component gas in the sample gas based on the first measurement signal. On the other hand, when the concentration of only the converted luminous component is calculated, the measurement signal calculating unit 31 calculates the concentration of the converted luminous component based on the difference between the second measurement signal and the first measurement signal. This is because the third detection signal contains not only the signal component based on the light emission by the interaction between the converted luminous component and the luminescence inducing component but also the signal component based on the light emission by the interaction between the component gas and the luminescence inducing component.

As described above, by calculating the first measurement signal and the second measurement signal based on the difference between the first detection signal and the second detection signal and based on the difference between the third detection signal and the second detection signal, respectively, in the measurement signal calculating unit 31, the first measurement signal and the second measurement signal without the signal component based on the reaction light generated by nitrogen monoxide (NO) as the secondary products can be calculated.

As the result, even when the concentration of the component gas (and/or the converted luminous component) is low (a few ppm in concentration), the concentration of the component gas and/or the converted luminous component can be calculated in high accuracy by using the first measurement signal and the second measurement signal described above.

After calculating the concentration of the component in step S9, the control unit 3 determines whether the measurement of the concentration should be terminated or not (step S10). If the control unit 3 determines that the measurement of the concentration should be terminated (if "Yes" in step S10), the gas analyzing apparatus 100 terminates the measurement of the concentration.

On the other hand, if the control unit 3 determines that the measurement of the concentration should be continued (if "No" in step S10), the process returns to step S5 and the measurement of the concentration is continued. Thus, the measurement of the concentration can be continued until the control unit 3 determines that the measurement should be terminated.

It should be noted that, as shown in FIG. 6B, after calculating the concentration of the component in step S9, the luminescence inducing component generation control unit 35 may adjust the discharge interval based on the calculated concentration of the component (the component gas and/or the converted luminous component) (step S10 of FIG. 6B).

For example, when the discharge interval is set to the first interval in step S2 and the concentration of the component gas (and the converted luminous component) increases and becomes larger than the predetermined concentration, the luminescence inducing component generation control unit 35 may reduce the discharge interval to the second interval.

Conversely, when the discharge interval is set to the second interval in step S3 and the concentration of the component gas (and the converted luminous component) in the sample gas decreases and becomes equal to or lower than the predetermined concentration, the luminescence inducing component generation control unit 35 may increase the discharge interval to the first interval.

Furthermore, when the discharge interval is set to the first interval in step S2 and the concentration of the component gas (and the converted luminous component) in the sample gas varies to the concentration equal to or lower than the predetermined concentration, the luminescence inducing component generation control unit 35 may change the discharge interval arbitrarily based on the calculated concentration of the component.

Thus, the amount of the generation of the secondary products and the luminescence inducing component (ozone ($O_3$)) can be adjusted appropriately based on the concentration of the component gas in the sample gas.

(3) Other Embodiments

The above described one embodiment of the present invention, but the present invention is not limited to the abovementioned embodiment, and it is understood that variations and modifications may be effected without departing from the spirit and scope of the invention. In particular, a plurality of the embodiments and modified examples described in the present specification can be arbitrarily combined as needed.

(A) Another Embodiment of the Introducing Pattern of Gas

In the gas analyzing apparatus 100 according to the first embodiment, as shown in FIG. 7, the first mixture gas, which is the mixture gas of the dilution gas and the sample gas, and the second mixture gas, which is the mixture gas of the dilution gas and the converted sample gas, are alternately introduced into the reaction unit 11. However, the introducing pattern of gas is not limited to the above.

For example, the standard gas and the second mixture gas may be alternately introduced into the reaction unit 11. In this case, the second switching control signal is always $S_{2ON}$ in signal value during the operation of the gas analyzing apparatus 100. In addition, only the second detection signal and the third detection signal are outputted as the detection signals.

Thus, the total concentration of the component gas and the converted luminous component (for example, the concentration of all nitrogen oxides ($NO_x$)) can be measured.

Or, the standard gas and the first mixture gas may be alternately introduced into the reaction unit 11. In this case, the second switching control signal is always zero in signal value during the operation of the gas analyzing apparatus 100. In addition, only the first detection signal and the second detection signal are outputted.

Thus, the concentration of only the component gas (for example, nitrogen monoxide (NO)) in the sample gas can be specifically measured.

The gas analyzing apparatus according to the present invention can be widely applied to the gas analyzing apparatus using CLA method.

What is claimed is:

1. A gas analyzing apparatus for measuring a concentration of a component gas in a sample gas using a chemical luminescence analysis method, the gas analyzing apparatus comprising:
    a gas analyzing unit comprising a sample gas introducing unit that introduces the sample gas and a standard gas, and receives a luminescence inducing gas, and further comprising a light detector configured to output a detection signal based on an intensity of a reaction light, the reaction light being generated by interaction between the component gas and a luminescence inducing component in the luminescence inducing gas;
    a luminescence inducing component generating unit configured to generate the luminescence inducing gas by electric discharge and connected to the gas analyzing unit to introduce the generated luminescence inducing gas into the gas analyzing unit, the electric discharge being generated repeatedly at a discharge interval, the discharge interval being determined based on the concentration of the component gas; and
    a measurement signal calculating unit coupled to the gas analyzing unit and the luminescence inducing component generating unit and programmed to calculate a first measurement signal for measuring the concentration of the component gas based on a first detection signal and a second detection signal, the first detection signal being outputted when the sample gas and the luminescence inducing gas are introduced into the gas analyzing unit, and the second detection signal being outputted when the standard gas and the luminescence inducing gas are introduced into the gas analyzing unit.

2. The gas analyzing apparatus according to claim 1, wherein the discharge interval is adjusted in accordance with the concentration of the component gas when the concentration of the component gas is equal to or less than a predetermined concentration.

3. The gas analyzing apparatus according to claim 1, wherein the standard gas and the sample gas are alternately introduced into the gas analyzing unit in a first period.

4. The gas analyzing apparatus according to claim 1, wherein a first mixture gas is introduced into the gas analyzing unit when the sample gas is introduced, the first mixture gas being a mixture of the sample gas and a dilution gas.

5. The gas analyzing apparatus according to claim 1, wherein the sample gas introducing unit comprises a conversion unit configured to generate a converted sample gas from the sample gas, the converted sample gas further including a converted luminescence component which emits light when interacting with the luminescence inducing component,
    wherein the gas analyzing unit is configured to output a third detection signal when the converted sample gas and the luminescence inducing gas are introduced into the gas analyzing unit, and
    the measurement signal calculating unit is configured to calculate a second measurement signal for measuring a concentration of the converted luminescence component based on the third detection signal and the second detection signal.

6. The gas analyzing apparatus according to claim 5, wherein the standard gas and the converted sample gas are alternately introduced into the gas analyzing unit in the first period.

7. The gas analyzing apparatus according to claim 5, wherein the sample gas and the converted sample gas are alternately introduced into the gas analyzing unit in a second period.

8. The gas analyzing apparatus according to claim 5, wherein a second mixture gas is introduced into the gas analyzing unit when the converted sample gas is introduced, the second mixture gas being a mixture of the converted sample gas and the dilution gas.

9. The gas analyzing apparatus according to claim 1, wherein the discharge interval is set based on a measured concentration of the component gas, and
    the discharge interval set when the measured concentration is equal to or lower than a predetermined concentration is larger than that when the measured concentration is more than the predetermined concentration.

10. The gas analyzing apparatus according to claim 1, wherein the discharge interval is set based on a range of a measurable concentration of the component gas, the discharge interval being set larger when the range of the measurable concentration is equal to or lower than a predetermined concentration than when the range of the measurable concentration is more than the predetermined concentration.

* * * * *